(12) United States Patent
Okazaki et al.

(10) Patent No.: US 6,719,721 B1
(45) Date of Patent: Apr. 13, 2004

(54) SAFETY PORT NEEDLE ASSEMBLY

(76) Inventors: Elizabeth Okazaki, One Broadway South, #305, Tacoma, WA (US) 98402; Richard Okazaki, 407 S. 306th St., Federal Way, WA (US) 98003; Paul Okazaki, 7953 4th Ave. SW., Seattle, WA (US) 98106

( * ) Notice: Subject to any disclaimer, the term of this patent is extended or adjusted under 35 U.S.C. 154(b) by 0 days.

(21) Appl. No.: 09/695,122

(22) Filed: Oct. 23, 2000

(51) Int. Cl.[7] ............................................... A61M 5/00
(52) U.S. Cl. .................... 604/110; 604/239; 604/272
(58) Field of Search ................................ 604/110, 177, 604/192, 239, 263, 264, 272, 890.1, 164.05, 64.05, 135, 232, 187, 223, 233, 224, 218, 228; 222/153.1, 562; 128/919

(56) References Cited

U.S. PATENT DOCUMENTS

| | | | | |
|---|---|---|---|---|
| 4,002,174 A | * | 1/1977 | Reed et al. ................. 604/117 |
| 5,021,057 A | | 6/1991 | Byrne, Jr. .................. 606/107 |
| 5,135,509 A | * | 8/1992 | Olliffe ...................... 604/192 |
| 5,156,426 A | | 10/1992 | Graves ....................... 294/1.1 |
| 5,342,311 A | | 8/1994 | Dirina ....................... 604/116 |
| 5,486,163 A | * | 1/1996 | Haynes ...................... 604/192 |
| 5,496,346 A | * | 3/1996 | Horzewski et al. ....... 604/164.05 |
| 5,620,419 A | | 4/1997 | Lui et al. ................... 604/116 |
| 5,669,889 A | * | 9/1997 | Gyure et al. ............... 128/919 |
| 5,693,022 A | * | 12/1997 | Haynes ...................... 604/192 |
| 5,797,954 A | | 8/1998 | Shaffer et al. ............. 606/201 |
| 5,858,001 A | * | 1/1999 | Tsals et al. ................. 604/135 |
| 6,120,482 A | * | 9/2000 | Szabo ........................ 128/919 |
| 6,280,401 B1 | * | 8/2001 | Mahurkar ................... 128/919 |

OTHER PUBLICATIONS http://www.deltec.com Dec. 2, 2002 Deltec, Inc. web site.

* cited by examiner

*Primary Examiner*—Brian L. Casler
(74) *Attorney, Agent, or Firm*—Dean A. Craine

(57) ABSTRACT

A safety port needle assembly used to connect an IV line to an implanted port needle receiving port. The assembly includes an L-shaped port needle with an integrally attached horizontal leg member, a vertical leg member, an elongated, fixed main body and a pivotally attached needle arm. The horizontal leg member is longitudinally aligned and attached to the needle arm. The vertical leg member extends downward perpendicular to the longitudinal axis of the needle arm. A channel is formed in the main body that enables the needle arm to rest longitudinally against the main body. A bore is also formed in the main body so that the vertical leg member may extend downward through the main body. Formed near the distal end of the main body is a pair of laterally extended wings.

17 Claims, 3 Drawing Sheets

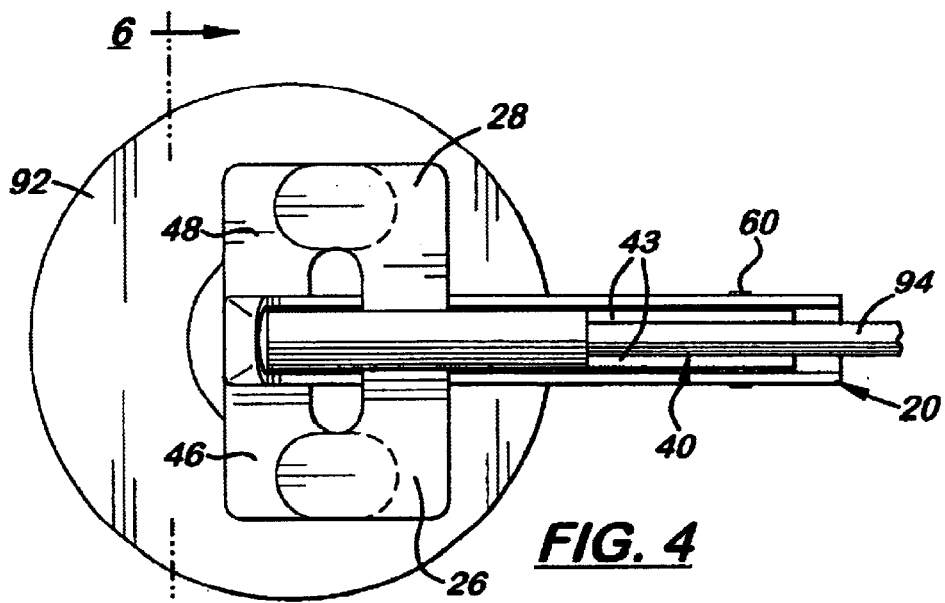
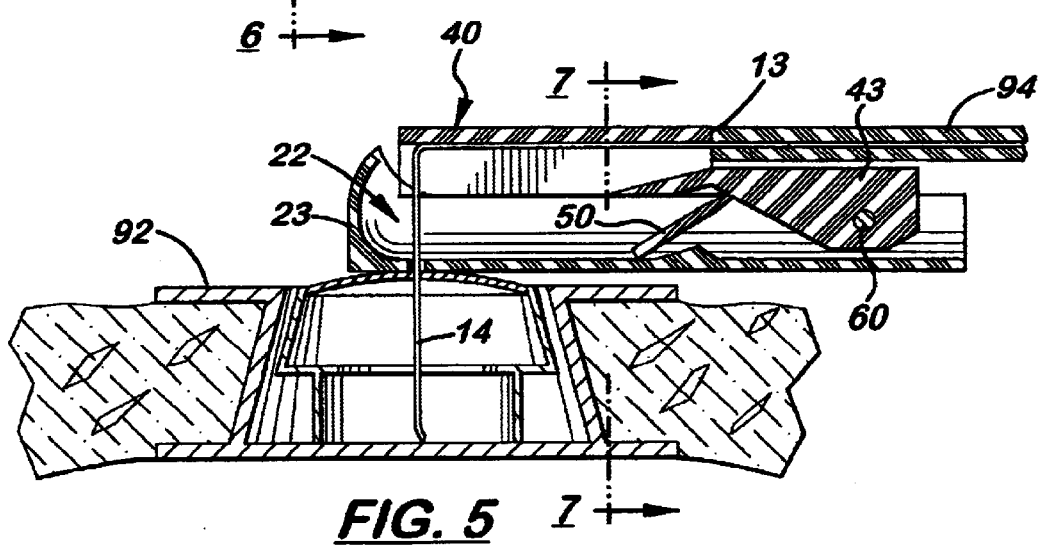
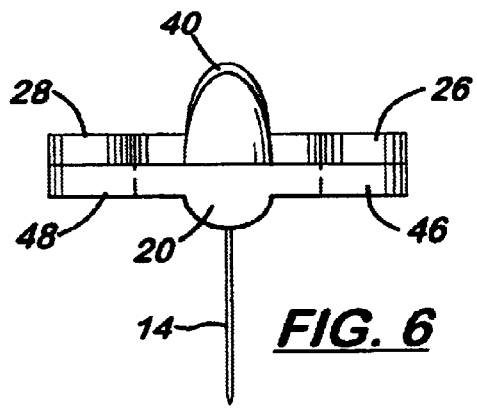
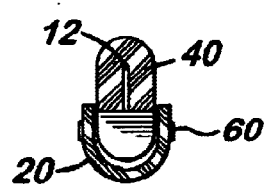

SAFETY PORT NEEDLE ASSEMBLY

BACKGROUND OF THE INVENTION

1. Field of the Invention

The present invention relates generally to the field of body entering conduits, and, more particularly, to conduits having protective levers to prevent accidental punctures.

2. Description of the Related Art

Medications are commonly administered by injection or continuous infusion into an implanted port, known as a vascular access port (VAP). VAPs are typically used in patients who need intermittent long-term I.V. therapy but can't use an external central venous catheter.

In order to administer medication through the port, access through the port must be obtained by carefully inserting a non-coring bent needle known as a Huber needle into the silicone injection septum located in the port. During the procedure, known as "accessing the port", the nurse or I.V. therapist is required to palpate and stabilize the port under the skin between his or her thumb and forefinger. While holding the Huber needle like a dart, at a 90-degree angle over the septum, the needle is pushed through the skin until it hits the needle stop located at the back of the septum.

Complications such as blockage, burning sensation, or when the central venous access is no longer required may occur that require the Huber needle to be removed, or "deaccessed" from the port. When "de-accessing" the port, the nurse or I.V. therapist must grab the end of the Huber needle with one hand and palpate the port under the skin between his or her finger with the other hand. The needle is then pulled upward with considerable force, removing it from the septum. After the needle is removed, the nurse or I.V. therapist must quickly deposit the needle in a safe location so that his or her hands may be used to stop any bleeding or provide additional treatment.

Because the nurse or I.V. therapist must stabilize the port between his or her fingers while the Huber needle is pushed or pulled from the port, accidental puncture sometimes occurs. Also, because the old needle may be quickly deposited, placing the old needle into the opening of a Sharps container can lead to accidental skin punctures.

What is needed is a safety port needle assembly that prevents accidental punctures when accessing and de-accessing a VAP and that completely covers the sharp end of the contaminated needle after it has been de-accessed from the port assembly.

SUMMARY OF THE INVENTION

It is an object of the present invention to provide a safety port needle assembly that reduces the risk of needle stick injury when accessing and de-accessing a VAP. It is a further object of this invention to provide a safety port needle assembly that is easy to use.

It is a further object of the present invention to provide a safety port needle assembly that fully contains the sharp end of the contaminated needle after de-accessing from the VAP.

These and other objects of the present invention are met by a safety port needle assembly used to connect an IV line to an implanted port needle receiving port. The assembly includes an L-shaped port needle with an integrally attached horizontal leg member and a vertical leg member. The horizontal leg member is disposed inside an elongated needle arm that is pivotally attached at one end to an elongated main body. The vertical leg member is perpendicularly aligned and extends downward from the distal end of the needle arm. A channel is formed in the main body that enables the needle arm to nest longitudinally inside the main body. A bore is also formed in the main body that enables the vertical leg member to extend downward through the main body when the needle arm is longitudinally aligned with the main body. Located in front of the bore is a pocket space which receives the tip of the port needle when extended above the bore. Also, formed near the distal end of the main body is a pair of laterally extended wings that enable a healthcare worker to securely hold the main body over the implant port using his or her fingers.

Disposed between the needle arm and the main body is an upward rotation limiting means that prevents the needle arm from being rotated upward excessively so that the tip of the needle is exposed. In the preferred embodiment, the upward rotating limiting means is a beveled surface formed on the needle arm that presses against the main body and prevents the needle arm from pivoting upward beyond a desired angle. Also provided is an optional downward rotation limiting means that provides the needle arm from being accidentally rotated downward after being rotated upward to prevent punctures. Also attached to the distal end of the needle arm is an optional pair of laterally extended wings that enables the needle arm to be easily rotated by the healthcare worker.

During use, an IV tube is connected to the proximal end of the horizontal leg member that extends rearward from the proximal end of the needle arm. The tip of the vertical leg member is then inserted into the implant port so that the second pair of wings is positioned directly against the patient's skin surround the implant port. The needle assembly can then be used to deliver fluids to the implant port. When de-accessing the implant port, the healthcare worker places the fingers of one hand over the first pair of wings to stabilize the main body over the implant port. The healthcare worker then grasps the second pair of wings with the fingers of the opposite hand, and lifts upward. As the second pair of wings is lifted, the needle arm pivots upward over the main body. When the needle arm pivots a sufficient distance, as determined by the length of the vertical leg of the port needle and the relative angle of the beveled surface, the tip of the vertical leg member extends above the bore on the main body. As the needle arm is pivoted rearward, a rearward directed force is applied to the vertical leg member. When the distal end of the vertical leg member extends past the bore, the vertical leg member snaps forward so that it is perpendicularly aligned with the horizontal member. When the vertical leg member snaps forward, it is received by the pocket space formed on the main body to further protect against accidental punctures.

There as thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

DESCRIPTION OF THE DRAWINGS

FIG. 4 is a top plan view of the safety port needle assembly shown in a closed position.

FIG. 5 is a sectional, left side elevation view of the safety port needle assembly shown in a closed position.

FIG. 6 is an end sectional elevation view of the safety port needle assembly taken along line 6—6 in FIG. 4.

FIG. 7 is a sectional end view of the needle arm taken along line 7—7 in FIG. 4.

DESCRIPTION OF THE PREFERRED EMBODIMENT(S)

Disclosed herein is a safety port needle assembly, generally referenced as 10 in the accompanying Figures., used to connect an I.V. line 94 to an implanted port needle receiving port 92 attached to a patient 90. More specifically, the needle assembly 10 is designed to prevent accidental punctures in accessing and de-accessing an implant port 92.

Figure 3:
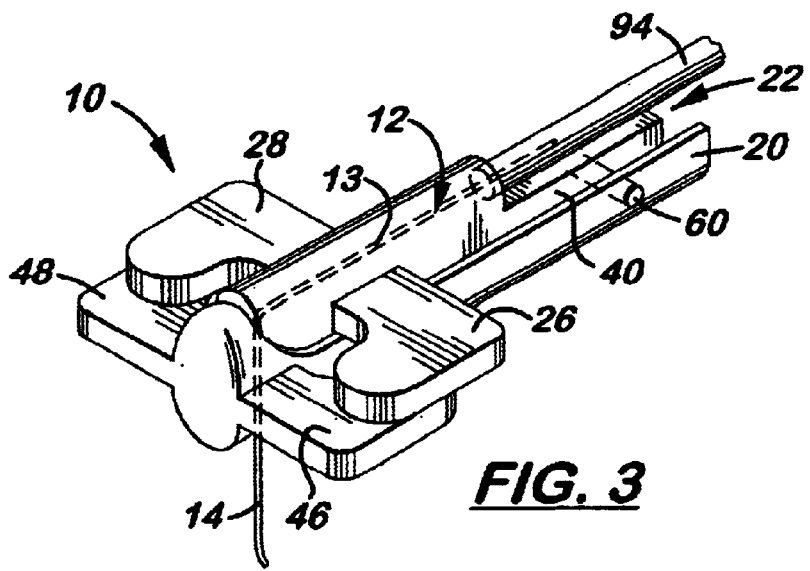
FIG. 3 is a perspective view of the safety port needle assembly.

The needle assembly 10 includes an L-shaped port needle 12 similar to a Huber needle with an integrally attached horizontal leg member 13 and a vertical leg member 14. The horizontal leg member 13 of the port needle 12 is longitudinally aligned and attached to a pivoting needle arm 40. The vertical leg member 14 extends downward perpendicular to the longitudinal axis of the needle arm 40. A channel 22 is formed along the entire length of the main body 20 that enables the needle arm 40 to rest partially inside the main body 20 when folded downward over the main body 20, as shown in FIGS. 3–5. A bore 24 is also formed in the main body 20 so that the vertical leg member 14 of the needle 12 may extend downward through the main body 20. Located in front of the bore 24 is a pocket space 23 which receives the tip of the port needle when extended above the bore. Formed near the distal end of the main body 20 is a first pair of laterally extended wings 26, 28.

Figure 8:
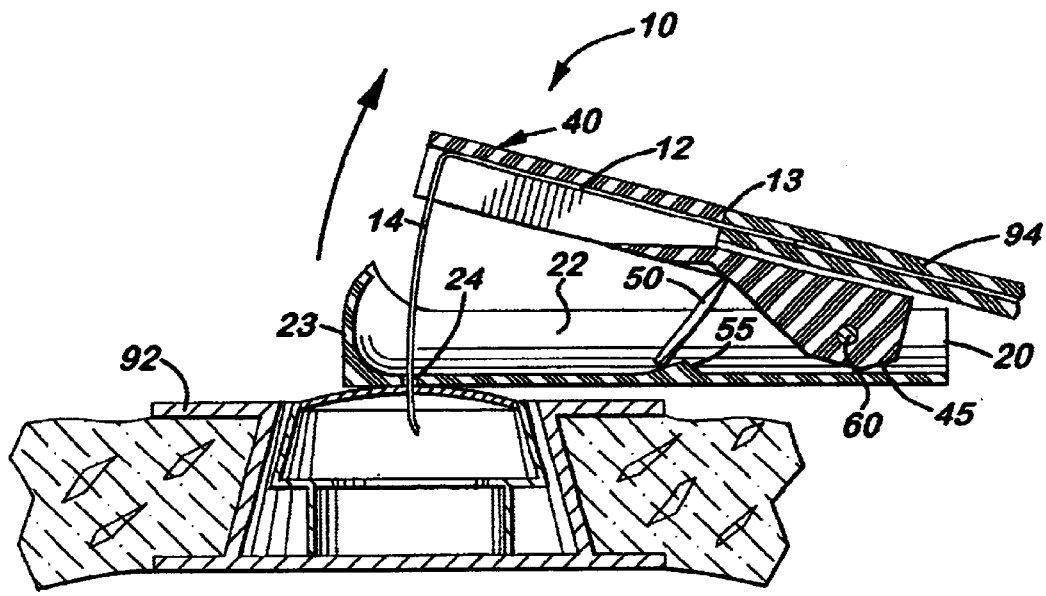
FIG. 8 is a partial, sectional, side elevational view of the safety port needle assembly showing it in an open position.
Figure 9:
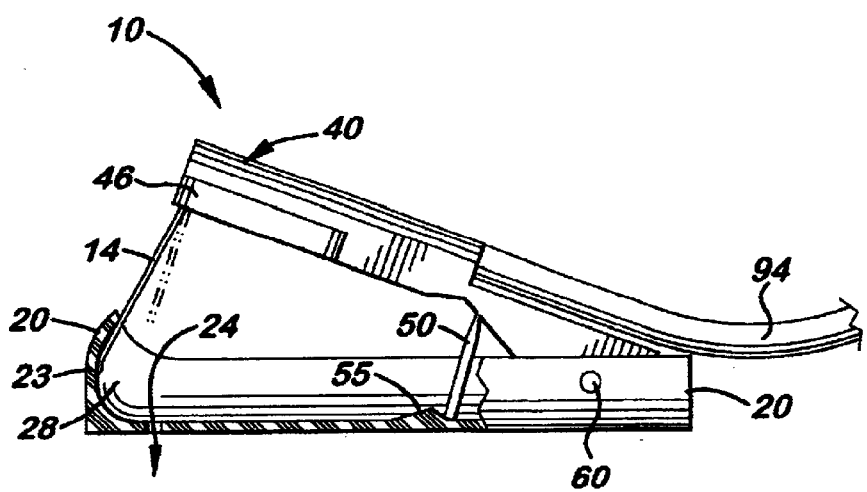
FIG. 9 is a partial, sectional side elevational view of the safety port needle assembly showing the needle in a locked position.

The needle arm 40 is pivotally attached at its proximal end via a transversely aligned pin 60 located near the proximal end of the main body 20. Formed on the bottom surface of the rear section of the needle arm 40 is a beveled surface 45 and acts as a stop surface to prevent the needle arm 40 from pivoting upward beyond a desired angle, as shown in FIGS. 8 and 9. In the preferred embodiment, the bevel surface 45 is aligned at approximately thirty degrees above the horizontal axis. Also attached near the distal end of the needle arm 40 is a second pair of laterally extended wings 46, 48. When placed in a closed position, the second pair of laterally extending wings 46, 48 are offset and stacked above the first pair of laterally extending wings 26, 28 as shown in FIG. 3.

Disposed between the needle arm 40 and the main body 20 is an optional downward rotation limiting means that prevents the needle arm from being accidentally rotated downward after being rotated upward to prevent punctures. In the preferred embodiment, the downward rotation limiting means a longitudinally aligned arm 50 pivotally attached to the bottom surface of the rear section 43 on the needle arm 40. In the preferred embodiment, the arm 50 integrally attached to the rear section 43 with a thin plastic layer that enables the arm 50 to pivot over the lower surface of the rear section 43. Formed on the inside surface of the main body 20 is a lip 55 which acts as a stop surface when the arm 50 is pulled rearward over the lip 55. The lip 55 prevents the arm 50 from sliding forward and preventing the needle arm 40 from pivoting downward.

As mentioned above, formed on the distal end of the main body 20 in front of the bore 24 is a narrow, slightly curved pocket space 23 designed to capture the tip of the port needle 12 when extended beyond the bore 24.

In the preferred embodiment, the main body 20 is made of FDA approved plastic and measures approximately 1¾ inch in length and ¼ inch in width. The port needle 12 is 19–22 gauge needle and with the horizontal leg 13 and vertical leg 14 measuring approximately 1 inch and 1¼ inches in length, respectively. The needle arm 40 measures approximately 1¼ inches in length and 3/16 inch in width. The first pair of wings 26, 28 measures approximately ½ inch in length and width. The second pair of wings 46, 48 measures approximately ½ inch in length and width.

Figure 1:
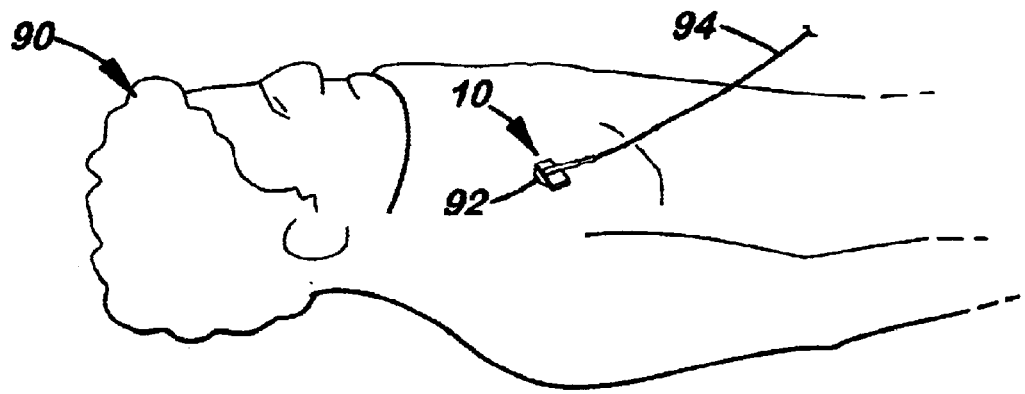
FIG. 1 is perspective view of a patient showing the safety port needle assembly installed.
Figure 2:
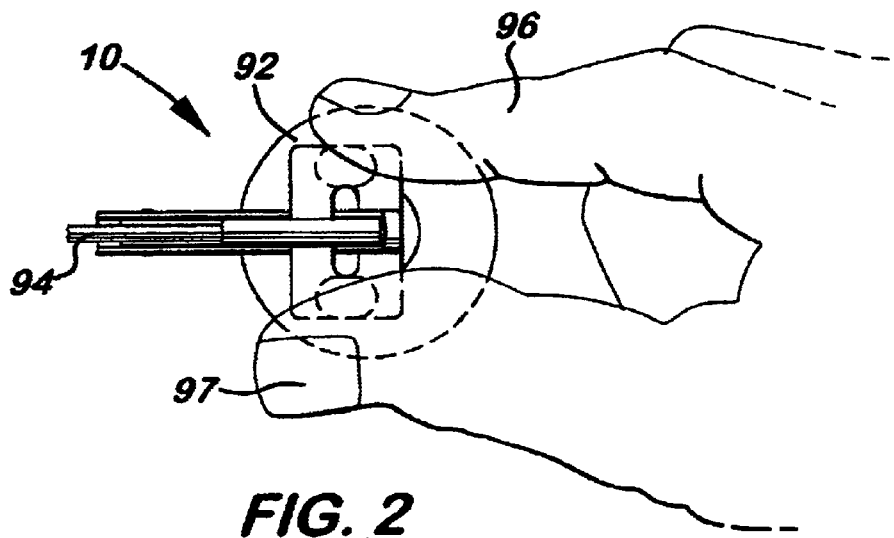
FIG. 2 is a top plan view of the safety port needle assembly being held in position by the user's fingers.

During use, an IV tube 94 is connected to the proximal end of the horizontal leg member 13 of the port needle 12 that extends rearward from the proximal end of the needle arm 40. The distal end of the vertical leg member 14 is then inserted into the implant port 92 so that the first pair of wings 26, 28 is positioned directly against the patient's skin adjacent to the implant port 92. The needle assembly 10 can then be used to deliver fluids to the implant port 92. When de-accessing the implant port 92, the healthcare provider places the fingers 96, 97 of one hand over the first pair of wings 26, 28, as shown in FIG. 2, grabs the second pair of wings, 46, 48 with the fingers of the opposite hand (not shown), and lifts upward. As the second pair of wings 46, 48 is lifted, the main body 20 remains horizontally disposed over the implant port 92 and the needle arm 40 pivots upward. When the needle arm 40 pivots approximately 30 degrees, the tip of the port needle 12 extends above the bore 24 on the main body 20 and snaps forward into the pocket space 23 formed on the main body 20.

Further, the purpose of the foregoing Abstract is to enable the U.S. Patent and Trademark Office worker, patent bar practitioners, and the general public, to determine quickly from a cursory inspection the nature and essence of the technical disclosure of the application. The Abstract is neither intended to define the invention of the Application, which is measured by the Claims, nor is it intended to be limiting as the scope of the invention in any way.

In compliance with the statute, the invention described herein has been described in language more or less specific as to structural features. It should be understood, however, that the invention is not limited to the specific features shown, since the means and construction shown, comprised only of the preferred embodiments for putting the invention into effect. The invention is therefore claimed in any of its forms or modifications within the legitimate and valid scope of the amended claims, appropriately interpreted in accordance with the doctrine of equivalents.

We claim:

1. A safety port needle assembly, comprising:
   a. an elongated main body having distal and proximal ends and a longitudinally aligned channel formed therein and a bore;
   b. a first pair of wings perpendicularly attached to said distal end of said main body;
   c. a needle arm longitudinally aligned with said main body, said needle arm being pivotally attached at one end to the proximal end of said main body, said needle arm also including a second pair of wings enabling said needle arm to be manually lifted and rotated;
   d. a port needle having a longitudinal leg and a vertical leg, said horizontal leg being attached to said needle arm and said vertical leg extending through said bore of said main body when said needle arm is longitudinally aligned over said main body, and;

e. a downward rotation limiting means located between said needle arm and said main body to prevent said needle arm from being rotated downward over said main body after being rotated upward and preventing punctures, and;

f. a pivoting arm formed on said needle arm and a lip formed on said main body which engage to prevent downward rotation of said needle arm after said needle arm is pivoted rearward.

2. The safety port needle assembly, as recited in claim 1, further including a stop surface formed on said needle arm to prevent excessive rearward rotation of said needle arm over said main body.

3. A safety port needle assembly, as recited in claim 2, wherein said channel is sufficient in size and shape to allow said needle arm to nest longitudinally inside said main body when pivoted downward over said main body.

4. A safety port needle assembly, as recited in claim 1, wherein said channel is sufficient in size and shape to allow said needle arm to nest longitudinally inside said main body.

5. A safety port needle assembly, comprised of the following:

a. an elongated main body, said main body having distal and proximal ends and a longitudinally aligned channel formed therein and a bore formed near said distal end;

b. a first pair of wings perpendicularly aligned and attached to said main body;

c. a needle arm longitudinally aligned with said main body, said needle arm being pivotally attached at one end to said proximal end of said main-body, said needle arm also including a second pair of wings enabling said needle arm to be manually lifted and pivoted rearward over said main body;

d. a port needle having a horizontal leg and a vertical leg, said horizontal leg being attached to said needle arm and said vertical leg extending through said bore of said main body when said needle arm is longitudinally aligned over said main body;

e. a stop surface formed on said needle arm to prevent excessive rearward rotation of said needle arm; and;

f. a locking pivoting arm disposed between said needle arm and said main body which is automatically engaged to prevent downward rotation of said needle arm when said needle arm is pivoted rearward a desired distance.

6. A safety port needle assembly, as recited in claim 5, further including a gripping means attached to said needle arm to enable said needle arm to be gripped and pivoted rearward over said main body.

7. A safety port needle assembly, as recited in claim 5, wherein said channel is sufficient in size and shape to allow said needle arm to nest longitudinally inside said main body.

8. A safety port needle assembly, comprising:

a. a main body having opposite distal and proximal ends with a bore formed near said distal end;

b. a needle arm longitudinally aligned over said main body and pivotally attached at one end to said proximal end of said main body;

c. a port needle having a horizontal leg and a vertical leg, said horizontal leg being longitudinally aligned and attached to said needle arm and said vertical leg extending downward from said needle arm and through said bore on said main body when said needle arm is longitudinally aligned over said main body, and;

d. a space formed on said main body for receiving the tip of said port needle when said needle arm is pivoted rearward to remove said tip of said port needle from said bore on said main body.

9. The safety port needle assembly, as recited in claim 8, further including a lateral pair of wings attached to said main body.

10. The safety port needle assembly, as recited in claim 9, further including a pair of laterally extending wings attached to said needle arm.

11. The safety port needle assembly, as recited in claim 9, further including a stop surface formed on said needle arm to prevent excessive rearward rotation of said needle arm over said main body.

12. The safety port needle assembly, as recited in claim 9, further including a locking pivoting arm disposed between said needle arm and said main body which is automatically engaged to prevent downward rotation of said needle arm when said needle arm is pivoted rearward a desired distance.

13. The safety port needle assembly, as recited in claim 9, wherein said main body includes a longitudinally aligned channel in which said needle arm may nest when longitudinally aligned over said main body.

14. The safety port needle assembly, as recited in claim 8, further including a pair of laterally extending wings attached to said needle arm.

15. The safety port needle assembly, as recited in claim 8, further including a stop surface formed on said needle arm to prevent excessive rearward rotation of said needle arm over said main body.

16. The safety port needle assembly, as recited in claim 8, further including a locking pivoting arm disposed between said needle arm and said main body, said locking pivoting arm capable of being automatically engaged to prevent downward rotation of said needle arm when said needle arm is pivoted rearward a desired distance.

17. The safety port needle assembly, as recited in claim 8, wherein said main body includes a longitudinally aligned channel in which said needle arm may nest when said needle arm is longitudinally aligned over said main body.

* * * * *